United States Patent [19]
Marshall

[11] 4,079,518
[45] Mar. 21, 1978

[54] AMALGAM MIXING, MULLING AND DISPENSING SYRINGE

[75] Inventor: Thomas Donald Marshall, Clear Lake City, Tex.

[73] Assignee: Odyssey Corporation for Research and Development, Clear Lake City, Tex.

[21] Appl. No.: 701,502

[22] Filed: Jul. 1, 1976

[51] Int. Cl.² .............................................. A61C 5/04
[52] U.S. Cl. ...................................................... 32/60
[58] Field of Search ................................. 32/40 A, 60; 259/DIG. 20

[56] References Cited
U.S. PATENT DOCUMENTS
3,638,314  2/1972  Lopez ...................................... 32/60

*Primary Examiner*—Robert Peshock

*Attorney, Agent, or Firm*—Arthur M. Dula; Murray Robinson; Ned L. Conley

[57] ABSTRACT

The invention is a disposable syringe comprising a dispensing plunger, a mulling plunger, a mercury storage chamber, an alloy storage chamber, and a passage means between the chambers. Mercury and alloy are prepackaged in their respective chambers during manufacture. Use of the apparatus involves unblocking passage means thus allowing mercury and alloy to combine in a chamber. Mercury and alloy can then be mixed into amalgam by vibrating entire syringe. Mulling plunger compresses amalgam within chamber in which amalgam was mixed. Dispensing plunger then dispenses a portion of mulled amalgam through syringe and out its tip. Amalgam remaining in syringe can then be further mulled by additional compression with mulling plunger.

27 Claims, 7 Drawing Figures

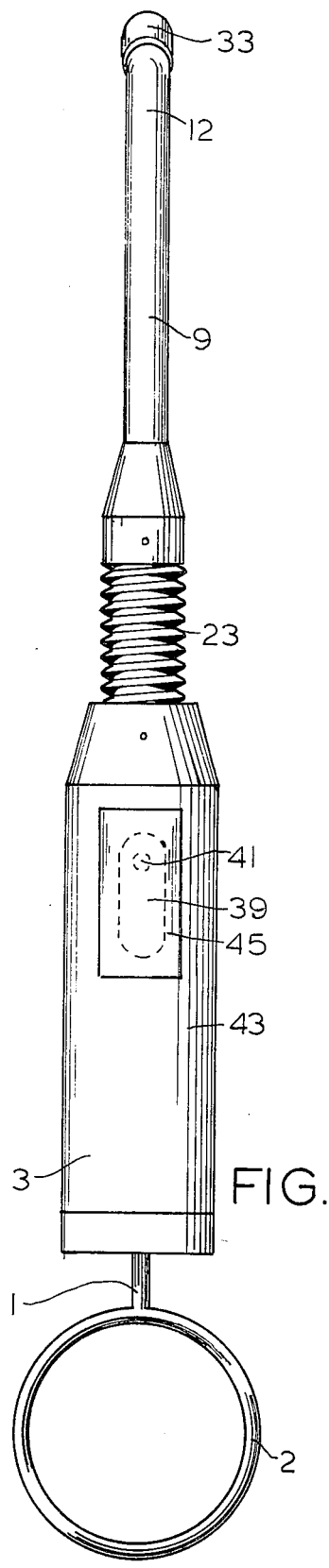
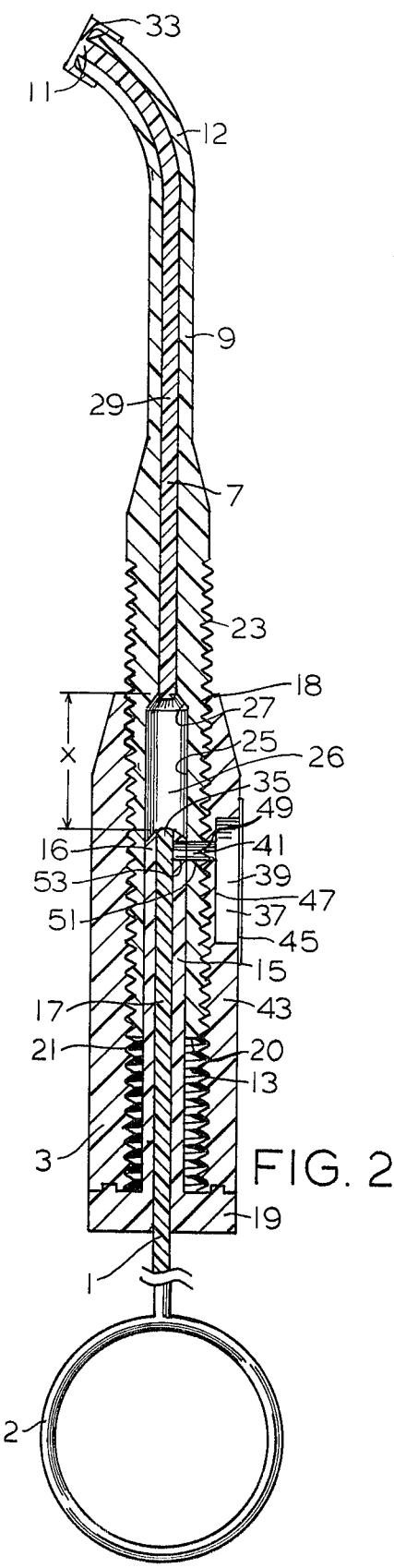

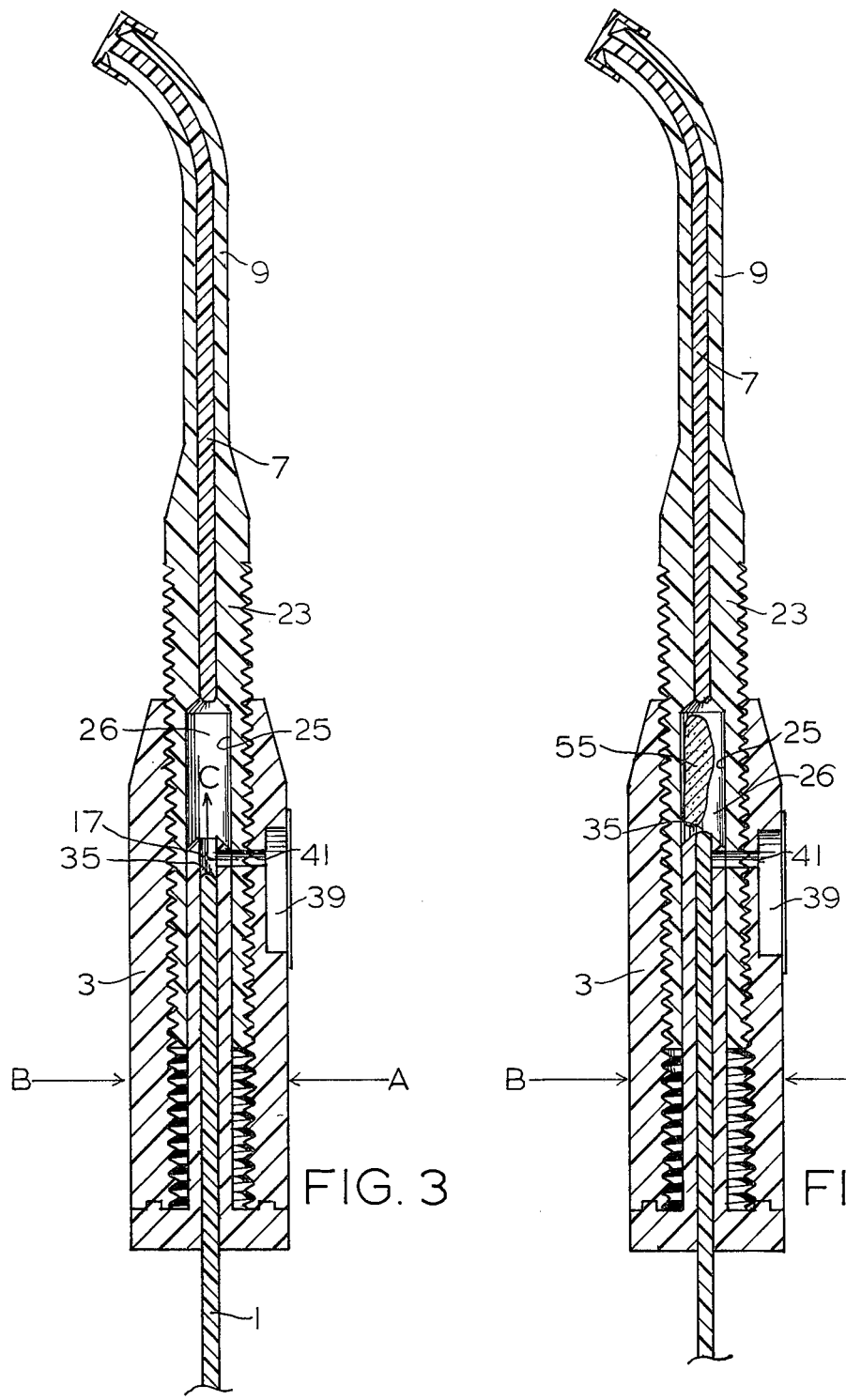

AMALGAM MIXING, MULLING AND DISPENSING SYRINGE

BACKGROUND OF THE INVENTION

1. Field of the Invention

The present invention relates generally to dental tools and equipment and more particularly to an apparatus for mixing, mulling and dispensing dental amalgam while preventing contamination of dental amalgam caused by contact with skin and while eliminating hazard of mercury poisoning.

2. Background of the Prior Art

In restoration of a tooth cavity, the dentist prepares cavity by drilling away decayed and soft portions of tooth in area of cavity. Then, a small portion of dental silver amalgam is prepared by mixing mercury with another metal, referred to here as "alloy", such as silver, copper, tin and zinc. Preparation of amalgam is commonly performed by a dental assistant while dentist is preparing cavity. Ratio of mercury to alloy portions mixed may be either excess mercury to alloy in the order of 7:5 or 8:5, or minimal mercury to alloy ratio of 1:1 or less. If excess mercury to alloy ratio is used, excess mercury must be expressed prior to condensing amalgam into cavity. Mercury expressing process is discussed in applicant's copending application entitled "Apparatus for Preventing Mercury Contamination." If minimal mercury to alloy ratio is used, amalgam is ready for application without the extra step of expressing excess mercury.

When amalgam is mixed such that each particle of alloy is coated with mercury and when excess mercury, if any, has been expressed, amalgam is loaded into a carrier. Tip of loaded carrier is then placed adjacent to prepared cavity and amalgam is forced from carrier and condensed into cavity with appropriate instruments.

Prior art teaches numerous devices and techniques designed to facilitate and improve effectiveness of this process. Many of these devices are directed toward facilitating removal of excess mercury when excess mercury to alloy ratio amalgam is used. Such devices are discussed in applicant's copending application entitled "Apparatus for Preventing Mercury Contamination" and that discussion is incorporated herein by reference.

As mentioned supra, necessity for removal of excess mercury may be avoided by use of minimal mercury to alloy ratio. This involves careful weighing of mercury and alloy portions to be mixed. Other methods of achieving minimal mercury to alloy ratio are use of factory preloaded and premeasured cartridges as taught by U.S. Pat. No. 3,612,352 to Smith, and devices that automatically measure portions of mercury and alloy as taught by U.S. Pat. No. 3,280,459 to Walker.

Devices directed to facilitating mixing of mercury and alloy are taught by U.S. Pat. Nos. 3,222,037 and 3,368,592 to Thiel, et al; 3,023,889 to Barr, and 3,828,434 to Mosch (trituration of mercury and alloy by way of mechanical vibration); U.S. Pat. No. 2,810,959 to Yates (paddle-shaped mixing tool for mixing amalgam in mortar); Walker, supra, and U.S. Pat. No. 3,611,573 (mixing amalgam in dispenser itself by mechanical mixing means disposed within dispenser).

Loading of prepared amalgam into dispenser has been facilitated by devices taught by both Thiel patents, supra, and U.S. Pat. No. 3,221,409 to Thiel, et al. (trituration process vibrates mixed amalgam from capsule into tube to be attached to dispenser); Mosch, supra, (tube itself is vibrated; tube then attached to dispenser); U.S. Pat. Nos. 1,188,417 to Dalbey, 3,521,356 to Newman, and 3,581,399 to Dragan (capsules or cartridges containing mixed amalgam loaded into dispenser); Smith, supra (mechanically shaping amalgam pellet for easy loading into dispenser). Loading of mixed amalgam into dispenser is avoided completely in Walker and Crawford, supra, in which mercury and alloy are mixed in dispenser itself.

Devices for facilitation of dispensing of amalgam are taught by U.S. Pat. No. 3,091,860 to Baughan (lever-action dispenser); U.S. Pat. No. 3,221,409 to Thiel, et al (ratchet-lever dispenser); U.S. Pat. No. 3,537,617 to Mendola (a second plunger slices off end of pellet forced into tube by a first plunger); Newman, supra, and U.S. Pat. No. 3,088,207 to Borsuk (pellet or plunger forced by compressed air); and Walker, supra (solenoid action).

Use of capsules, cartridges, and mixing in dispensers reduces opportunity of contamination of amalgam by way of contact with skin. This better assures a good filling of the cavity.

The prior art, however, has left two problems associated with the nature of amalgam and its constituents relatively unaffected. First, amalgam does not retain the form of a compact pellet or the like after mixing; instead, it tends to fall apart into many smaller particles and must be continually compacted or mulled during filling operation. This problem can severely impede the processes of loading a carrier, dispensing amalgam from carrier, and/or condensing amalgam into a prepared cavity. U.S. Pat. No. 2,716,816 to Braum teaches a device for mulling dental amalgam whereby contact between amalgam and skin is reduced. An advancement on mulling devices is taught in applicant's copending application entitled "Apparatus for Preventing Mercury Contamination". U.S. Pat. No. 3,222,037 to Thiel, et al., attempts to solve amalgam scattering problem by entrapping particles of amalgam in a dispenser tube. Even after entrapment in dispenser tube, amalgam is not mulled but remains in its separate and loose form.

Second, and probably most importantly mercury has been found to be a highly poisonous material. Poisoning can occur either through skin contact with liquid mercury or by breathing mercury vapor. A large number of articles have dealt with the ever-present danger of mercury contamination of dental operatories. See, e.g., Mantyla, *Protection of Dental Personnel Through Proper Mercury Hygiene,* DENTAL SURVEY (June 1973 58; Cedar, *Mercury Vapor: A Hazard in the Dentist's Office,* DENTAL STUDENT (February 1973) 28; Buchwald, *Using Mercury Safely,* DENTAL HYGIENE (July-August 1973) 231; Buchwald, *More About Mercury Hygiene,* Nixon and Rowbotham, *Mercury Hazards Associated With High Speed Mechanical Amalgamators,* BRITISH DENTAL JOURNAL (Oct. 5, 1971) 308; Borkowski and Mazza, *Mercury Contamination of the Dental Office and Central Air Conditioning,* NORTH CAROLINA DENTAL JOURNAL (Spring 1975) 13; Chandler, Rupp and Paffenbarger, *Poor Mercury Hygiene From Ultrasonic Amalgam Condensation,* 82 J.A.D.A. 553.

The present invention effectively eliminates any hazard of mercury contamination during the tooth restoration operation while permitting continual mulling of amalgam during actual filling operation. Furthermore, the present invention avoids step of removing excess mercury by factory preloading minimal mercury to alloy portions in syringe itself; avoids step of loading dispenser by providing for mixing of amalgam in dispenser itself; and facilitates dispensing by providing a dispenser of small size with simple, single-plunger dispensing action. Although present invention far surpasses capabilities of any device taught by prior art, it is less complex and less costly than many of the prior art devices.

SUMMARY OF THE PRESENT INVENTION

The invention is a disposable syringe in which constituent ingredients for dental amalgam are prepackaged during manufacture and are separately stored until immediately prior to use. Amalgam is mulled while in the syringe and is dispensed directly from syringe. The syringe comprises one chamber in which mercury is stored, a second chamber within which alloy is stored, a passage between the chambers, a mulling plunger and a dispensing plunger. Prior to use, passage is blocked. When passage is unblocked upon use, mercury and alloy are combined in one chamber and are mixed by vibration of entire syringe thus forming amalgam. Mulling plunger compresses amalgam within chamber in which amalgam is mixed and maintains compression pressure while dispensing plunger dispenses a portion of mulled amalgam. Mulling plunger can then further compact amalgam and dispensing plunger can dispense a second portion of amalgam. This procedure can be continued until operation is complete. Since mercury and amalgam are in a sealed system, mercury vapor contamination is prevented. Furthermore, mercury does not come into contact with hands. Proper disposal of syringe assures that syringe will not ultimately be burned in an incinerator. No carrier loading, capsule loading, or removal of excess mercury is required during use.

BRIEF DESCRIPTION OF THE DRAWINGS

FIG. 1 is an axial elevation of the preferred embodiment.

FIG. 2 is a sectional drawing of the preferred embodiment in the store position.

FIG. 3 is a sectional drawing of the preferred embodiment with dispensing plunger withdrawn so mercury may combine with alloy.

FIG. 4 is a sectional drawing of the preferred embodiment just after mixing of mercury and alloy and with dispensing plunger returned to store position.

DESCRIPTION OF THE PREFERRED EMBODIMENT

Figure 5:
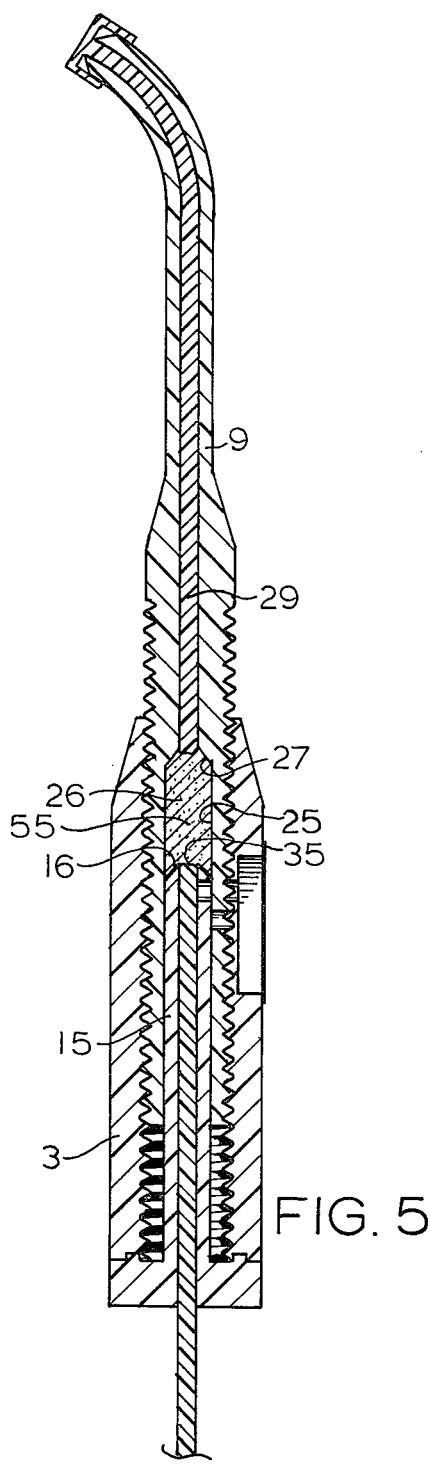
FIG. 5 is a sectional drawing of the preferred embodiment with the mixed amalgam compressed by the mulling plunger.

As seen in FIGS. 1 and 2, the preferred embodiment of the present invention resembles a syringe with a dispensing plunger 1 having finger rest 2 slidingly disposed within a syringe body 3 so as to force material into dispensing channel 7 within syringe tip 9, and out through opening 11 at extreme end 12 of tip 9. Tip 9 is curved at its extreme end 12 to facilitate dispensing of amalgam into a prepared cavity.

Syringe body 3 is a cylindrically-shaped internally threaded tube with body chamber 13 extending therethrough. Mulling plunger 15 having plunger passage 17 therethrough extends coaxially within chamber 13 and is secured to syringe body 3 by cap 19. Outer diameter of mulling plunger 15 is less than diameter of body chamber 13 thus leaving annular space 21 between mulling plunger 15 and internally-threaded wall of syringe body 3. Plunger 1 is slidably disposed within plunger passage 17 in a friction fit. Free end 16 of mulling plunger 15 is recessed from open end 18 of syringe body 3 by a distance X.

Tip 9 has externally threaded pin 23 adapted to be threadingly received by syringe body 3. Dispensing channel 7 within tip 9 has an enlarged portion 25 at the pin 23 end of tip 9 such that when pin 23 is threadingly received within syringe body 3 beyond a distance X, enlarged portion slidably engages mulling plunger 15 with a friction fit and pin 23 moves into annular space 21. Axial length of enlarged portion 25 is less than or equal to axial length of annular space 21 such that free end 16 of mulling plunger 15 meshes with annular shoulder 27 formed between enlarged portion 25 and remainder of dispensing channel 7 before end 28 of pin 23 abuts cap 19 when threading tip 9 into syringe body 3.

Remainder of dispensing channel 7 and plunger passage 17 have identical diameters. When pin 23 is received by body 3, the concentric arrangement of dispensing channel 7 within tip 9 and plunger passage 17 results in automatic alignment of dispensing channel 7 and plunger passage 17. Thus, plunger 1 may be pushed completely through plunger passage 17 and into dispensing channel 7. Plunger 1 has sufficient axial length to extend maximum distance from cap 19 to opening 11 at extreme end 12 of tip 9.

Plunger 1 is made of a material of sufficient flexibility to bend through curved extreme end 12 of tip 9.

In its store position as shown in FIG. 2, invention has two storage chambers. Alloy storage chamber 26 is formed in enlarged portion 25 between free end 16 of mulling plunger 15 and annular shoulder 27 of tip 9 when tip 9 has been screwed into body 3 by a distance greater than X. Dispensing channel 7 is sealed by flexible tip insert 29 which comprises sealing means 31 extending from opening 11 to annular shoulder 27 and is attached to tip cap 33 which secures tip insert 29 to tip 9 at extreme end 12. Plunger passage 17 is sealed by positioning plunger 1 such that plunger tip 35 is flush with free end 16 of mulling plunger 15.

Mercury storage chamber 37 comprises mercury reservoir 39 and mercury passage 41. Mercury reservoir 39 is formed by a recess in wall 43 of body 3. In the store position mercury reservoir 39 is covered by adhesive mercury reservoir seal 45 which seals mercury reservoir at outer periphery of body 3. Mercury passage 41 is a cylindrical passage extending from base 47 of mercury reservoir 39 through remainder of wall 43 of body 3 at 49 through radial width of pin 23 at 51, and through radial width of mulling plunger 15 at 53. In order for mercury passage to provide fluid communication from body 3 through mulling plunger 15 when tip 9 has been received by body 3 beyond a distance X, passage portions 49 and 53 in body 3 and mulling plunger 15, respectively, must be aligned with passage portion 51 in tip 9. Such alignment puts apparatus in appropriate store position. Mercury passage is sealed at periphery of plunger passage 17 by plunger 1 which, as mentioned supra, extends through plunger passage 17.

In assembling apparatus, tip insert 29 is inserted into tip 9 and secured in tip 9 by tip cap 33. Factory premeasured portion of alloy is then placed in enlarged portion 25 of dispensing channel 7. Body 3 is then screwed about tip 9 until mercury passage portions 49 and 53 align with mercury passage portion 51 in tip 9. Plunger 1 is then inserted into plunger channel 17 until plunger tip 35 is flush with free end 16 of mulling plunger 15. Plunger 1 is held in place by the friction fit in plunger passage 17. Main axis of apparatus is placed in horizontal position and premeasured portion of mercury is inserted into mercury reservoir 39. Premeasured portions of mercury and alloy may vary in actual amount so long as the ratio of mercury to alloy is minimal. The minimal ratio of mercury to alloy is that ratio that will result in mercury coating of every particle of alloy without resulting in excess mercury. The actual ratio will vary depending on the alloy used. Adhesive mercury reservoir seal 45 is then placed on body 3 so as to completely cover mercury reservoir 39. At this time, apparatus is in its store position and is ready for use by dentists. No further exposure of either mercury or amalgam will occur until amalgam is dispensed into a cavity.

Operation of apparatus involves withdrawing of plunger 1 just enough to open mercury passage 41 at plunger passage 17 as shown in FIG. 3. Mercury is then allowed to pass in direction of arrow C from mercury reservoir 39, through mercury passage 41 and plunger passage 17, and into enlarged portion 25 of dispensing channel 7. When all mercury is in enlarged portion 25, plunger 1 is returned to store position and apparatus is attached to a mechanical triturator commonly used in dental operatories. Triturator arms may be attached at points A and B on body 3 as shown in FIG. 3, and syringe is vibrated parallel to its main axis.

At completion of trituration, apparatus is removed from triturator. Immediately after mixing, amalgam will appear as shown at 55 in FIG. 4. As shown in FIG. 5, amalgam 55 is then mulled by threading body 3 farther on to pin 9 thus decreasing size of alloy chamber 26 and compacting amalgam between periphery of enlarged portion 25, annular shoulder 27, tip insert 29, free end 16 of mulling plunger 15, and plunger tip 35.

Figure 6:
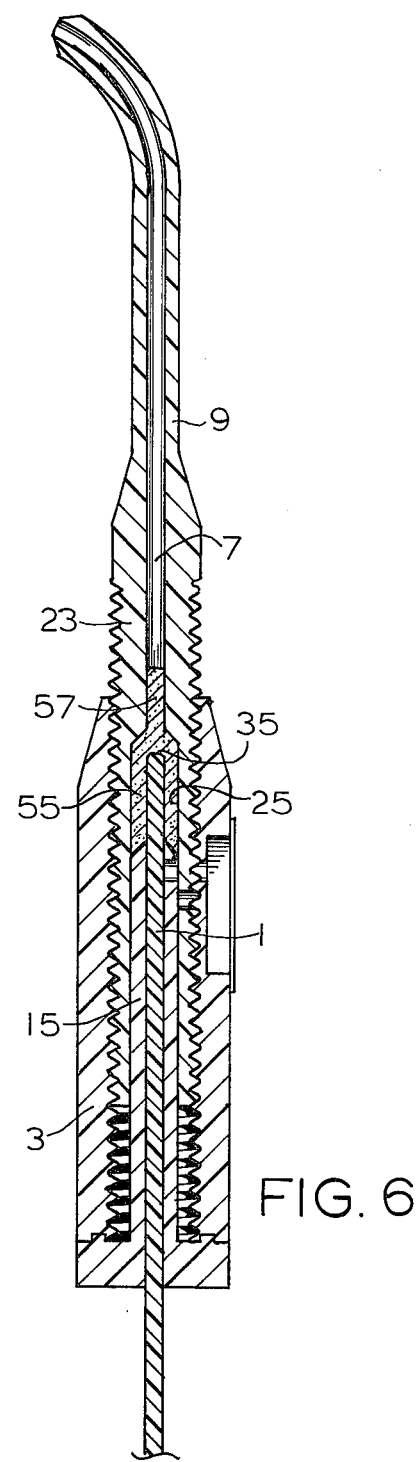
FIGS. 6 and 7 are sectional drawings of the preferred embodiment wherein mulled amalgam is being dispensed.
Figure 7:
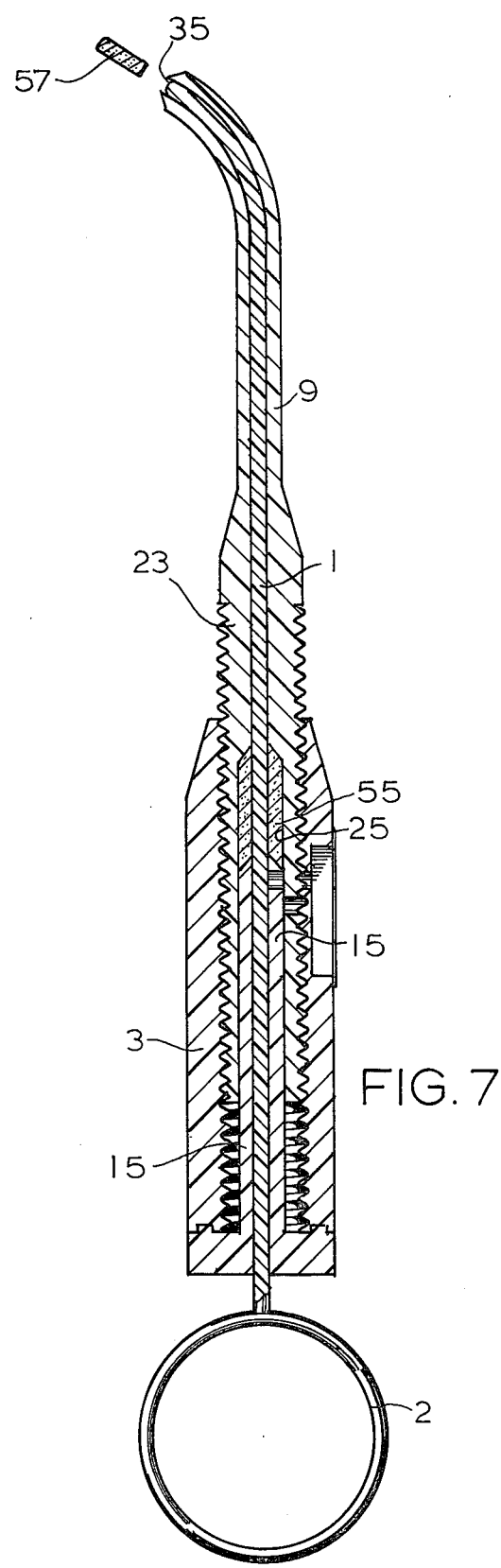

Tip insert 29 is then removed and a pellet 55 of amalgam is dispensed as shown in FIGS. 6 and 7. Plunger 1 is then withdrawn until plunger tip 35 is flush with free end 16 of mulling plunger 15. Tip insert 29 is replaced and amalgam is again mulled by further screwing body 3 onto tip 9. A second pellet of amalgam can then be dispensed. This process can be continued until operation is completed.

As seen in FIG. 2, annular shoulder 27 and free end 16 of mulling plunger 15 may be angled toward extreme end 12 of tip 9 to facilitate mulling. Further, if amalgam has sufficient plasticity after mixing, small diameter of the tip end of dispensing passage 7 allows for mulling without reinsertion of tip insert 29.

When operation is completed, apparatus can be separately disposed to assure that the unit is not ultimately burned in an incinerator. Because unit is disposable, no cleaning is necessary. Thus contamination of waste water is prevented.

Simplicity of invention assures small cost of manufacture thus assuring disposability. Apparatus may be manufactured of relatively inexpensive material such as nylon or delrin or other material commonly used in disposable syringes.

While a preferred embodiment of the present invention has been shown and described, modifications thereof can be made by one skilled in the art without departing from the spirit of the present invention.

I claim:

1. Syringe for mixing components of dental amalgam together, and for mulling and dispensing dental amalgam comprising:
   a first chamber for storing one of the components of dental amalgam;
   a second chamber for storing another of the components of dental amalgam;
   passage means for connecting said first chamber to said second chamber;
   valve means for variably blocking said passage means;
   dispensing passage in fluid communication with said first chamber;
   mulling means adjacent to said first chamber for reducing volume of said first chamber; and
   first plunger means adapted to pass through said first chamber and into said dispensing passage.

2. Syringe according to claim 1 wherein said valve means includes a portion of said first plunger means in cooperation with a portion of said mulling means.

3. Syringe for mixing, mulling and dispensing dental amalgam comprising:
   a storage chamber and a mixing chamber in fluid communication with one another;
   valve means for variably blocking said fluid communication between said chambers;
   dispensing passage in fluid communication with said mixing chamber;
   mulling means adjacent to said mixing chamber for reducing volume of said mixing chamber; and
   first plunger means adapted to pass through said mixing chamber and into said dispensing passage,
   wherein said mulling means is a second plunger means constituting a wall of said mixing chamber and said second plunger means is tubular in shape and has an axial plunger passage there through and said first plunger means is slidingly disposed within said plunger passage.

4. Syringe for mixing, mulling and dispensing dental amalgam according to claim 3 wherein said dispensing passage opens into the wall of said mixing chamber opposite said second plunger means and extends away from said mixing chamber along an extension of the axis of said second plunger means.

5. Syringe for mixing, mulling and dispensing dental amalgam according to claim 3 wherein said plunger means is said valve means.

6. Syringe for mixing, mulling and dispensing dental amalgam comprising:
   a storage chamber and a mixing chamber in fluid communication with one another;
   valve means for variably blocking said fluid communication between said chambers;
   dispensing passage in fluid communication with said mixing chamber;
   mulling means adjacent to said mixing chamber for reducing volume of said mixing chamber; and
   first plunger means adapted to pass through said mixing chamber and into said dispensing passage,
   wherein said mixing chamber is substantially tubular in shape and has an axis, said mulling means being a second plunger means constituting one wall of said mixing chamber and moving along said axis, and radial cross section of said second plunger means and radial cross section of said mixing chamber having relative size and shape such that second plunger means slides within said mixing chamber while providing a substantially sealing fit between said mixing chamber and said second plunger means.

7. Syringe for mixing, mulling and dispensing dental amalgam according to claim 6 wherein said second plunger means has a plunger passage there through;

said dispensing channel opening into said end of said mixing chamber opposite said second plunger means and extending from said mixing chamber coaxially with said mixing chamber and said second plunger means;

said first plunger means slidably disposed within said plunger passage whereby it may pass from said plunger passage, through said mixing chamber, and into said dispensing channel.

8. Syringe for mixing, mulling and dispensing dental amalgam according to claim 7 wherein said mixing chamber and said storage chamber are in fluid communication through a radial passage in said second plunger means and said plunger passage whereby said first plunger means is said valve means.

9. Syringe according to claim 1 wherein said dispensing channel has an open end constituting the tip of said syringe.

10. Syringe according to claim 1 wherein said syringe is disposable.

11. syringe for mixing, mulling and dispensing dental amalgam comprising:

a storage chamber and a mixing chamber in fluid communication with one another;

valve means for variably blocking said fluid communication between said chambers;

dispensing passage in fluid communication with said mixing chamber;

mulling means adjacent to said mixing chamber for reducing volume of said mixing chamber; and first plunger means adapted to pass through said mixing chamber and into said dispensing passage, wherein said valve means blocks said fluid passage means;

a premeasured portion of mercury is disposed in said storage chamber;

a premeasured portion of alloy is disposed in said mixing chamber;

said premeasured portions of said mercury to said alloy having a minimal mercury to alloy ratio;

said mixing chamber and said storage chamber being sealed from each other and from the ambient.

12. Syringe according to claim 1 wherein said syringe is adapted for attachment to a mechanical vibrator.

13. Syringe for mixing, mulling and dispensing dental amalgam comprising:

a tip having a tip channel therethrough;
a body having a body chamber therein;
a first plunger having a plunger passage therethrough;
said tip adjustably received in said body chamber;
said first plunger disposed in said tip channel;
a second plunger disposed in said plunger passage;
said tip channel and said first plunger forming a mixing chamber;

a storage chamber disposed in said body; fluid passage means for allowing fluid communication between said storage chamber and said mixing chamber; and valve means for variably blocking said fluid passage means thus variably restricting fluid communication between said storage chamber and said mixing chamber.

14. Syringe for mixing, mulling and dispensing dental amalgam according to claim 13 wherein said tip has a pin and said body has a box, said pin being threadingly received in said box.

15. Syringe for mixing, mulling and dispensing dental amalgam according to claim 13 wherein said body is substantially tubular in shape and said body chamber is coaxial with said body;

said first plunger coaxially disposed in said body chamber and having an external diameter smaller than diameter of said chamber whereby an annular shape is created between said body and said first plunger;

said tip being received in said annular space.

16. Syringe for mixing, mulling and dispensing dental amalgam according to claim 15 wherein said first plunger is rigidly secured to said body such that axial movement of said tip within said body causes axial movement of said first plunger within said tip passage.

17. Syringe for mixing, mulling and dispensing dental amalgam according to claim 16 wherein said tip has an externally theaded pin and said body has an internally threaded box, said pin being threadingly received in said box whereby as said pin is threaded into said box, said first plunger moves axially within said tip channel.

18. Syringe for mixing, mulling and dispensing dental amalgam according to claim 16 wherein said fluid passage means comprises a first portion and a second portion;

said first portion extending radially through the wall of said body;

said second portion extending radially through the wall of said tip;

fluid communication between said storage chamber and said mixing chamber occuring only when said first portion and said second portion are aligned by movement of said body about said tip whereby said walls of said body and said tip constitute said valve means.

19. Syringe for mixing, mulling and dispensing dental amalgam according to claim 16 wherein said tip channel is enlarged at the end corresponding to the end of the tip received by said body whereby an annular shoulder is formed between such enlarged portion of said tip channel and remainder of said tip channel;

said first plunger adapted to mesh with said annular ring;

said annular ring forming a wall of said mixing chamber.

20. Syringe for mixing, mulling and dispensing dental amalgam according to claim 19 wherein said first plunger seals opening of said dispensing channel at said enlarged portion;

said second plunger is slidable axially within said plunger passage and seals said plunger passage whereby said mixing chamber communicates with ambient only through said remainder of said tip channel; and said second plunger is aligned with said remainder of said tip channel such that it may be extended from said plunger channel, through said mixing chamber, past said annular shoulder and through said remainder of said tip channel.

21. Syringe for mixing, mulling and dispensing dental amlagam according to claim 20 wherein said fluid passage means extends radially through said body, said tip and said first plunger and said second plunger means is said valve means whereby as said second plunger is withdrawn within said plunger passage away from said mixing chamber and past opening of said fluid passage means in said first plunger, fluid communication between said storage chamber and said mixing chamber is unblocked.

22. Syringe for mixing, mulling and dispensing dental amalgam according to claim 19 wherein said remainder of said tip channel is blocked by a removable tip insert extending from said annular shoulder to end of said tip opposite said end within which said enlarged portion extends.

23. Syringe for mixing, mulling and dispensing dental amalgam according to claim 19 wherein said annular shoulder is beveled away from said enlarged portion.

24. Syringe according to claim 13 wherein said syringe is disposable.

25. Syringe for mixing, mulling and dispensing dental amalgam according to claim 13 wherein said valve means blocks said fluid passage means;
 a premeasured portion of mercury is disposed in said storage chamber;
 a premeasured portion of alloy is disposed in said mixing chamber;
 said premeasured portions of said mercury and said alloy having a ratio of one-to-one;
 said mixing chamber and said storage chamber being sealed from each other and from the ambient.

26. Syringe for mixing, mulling and dispensing dental amalgam according to claim 13 wherein said syringe is adapted for attachment to a mechanical vibrator.

27. Apparatus for mixing, mulling and dispensing dental amalgam comprising:
 a mixing chamber within which such amalgam is mixed;
 a storage chamber, said storage chamber and said mixing chamber being in variably blocked fluid communication with one another;
 a dispensing passage opening into said mixing chamber;
 first plunger means for compressing such amalgam within said mixing chamber, said first plunger means having a first plunger passage; and
 second plunger means for forcing such amalgam from said mixing chamber into said dispensing passage, at least a portion of said second plunger being slidingly disposed within said first plunger passage.

* * * * *

UNITED STATES PATENT OFFICE
CERTIFICATE OF CORRECTION

Patent No. 4,079,518      Dated March 21, 1978

Inventor(s) Thomas Donald Marshall

It is certified that error appears in the above-identified patent and that said Letters Patent are hereby corrected as shown below:

Column 2, line 50, after "1973", insert -- ) --.
Column 9, line 8, change "amlagan" to -- amalgam --.

Signed and Sealed this

Fifth Day of June 1979

[SEAL]

Attest:

RUTH C. MASON
Attesting Officer

DONALD W. BANNER
Commissioner of Patents and Trademarks